(12) United States Patent
Wright et al.

(10) Patent No.: US 11,197,634 B2
(45) Date of Patent: Dec. 14, 2021

(54) GEOSPATIAL BIOIMPEDANCE BIOSURVEILLANCE TOOL

(71) Applicants: Wayne C. A. Wright, Linton Maidstone (GB); John D. Kutzko, Pagosa Springs, CO (US)

(72) Inventors: Wayne C. A. Wright, Linton Maidstone (GB); John D. Kutzko, Pagosa Springs, CO (US)

(*) Notice: Subject to any disclaimer, the term of this patent is extended or adjusted under 35 U.S.C. 154(b) by 0 days.

(21) Appl. No.: 17/240,509

(22) Filed: Apr. 26, 2021

(65) Prior Publication Data
US 2021/0330253 A1 Oct. 28, 2021

Related U.S. Application Data

(60) Provisional application No. 63/016,475, filed on Apr. 28, 2020.

(51) Int. Cl.
| | |
|---|---|
| *A61N 1/36* | (2006.01) |
| *A61N 1/372* | (2006.01) |
| *A61B 5/00* | (2006.01) |
| *A61B 5/11* | (2006.01) |
| *A61B 5/0537* | (2021.01) |
| *A61B 5/25* | (2021.01) |

(52) U.S. Cl.
CPC .......... *A61B 5/4842* (2013.01); *A61B 5/0004* (2013.01); *A61B 5/0022* (2013.01); *A61B 5/0537* (2013.01); *A61B 5/1112* (2013.01); *A61B 5/25* (2021.01); *A61B 5/445* (2013.01); *A61B 5/4836* (2013.01); *A61B 5/6806* (2013.01); *A61B 5/6826* (2013.01); *A61B 5/6829* (2013.01); *A61B 5/6831* (2013.01); *A61B 5/6833* (2013.01); *A61B 5/742* (2013.01); *A61B 5/746* (2013.01)

(58) Field of Classification Search
CPC ....... A61B 5/204; A61B 5/021; A61B 5/0816; A61B 5/1118; A61B 5/14539; A61B 5/14551; A61B 5/224; A61B 5/4337; A61B 5/7282; A61B 5/746
See application file for complete search history.

(56) References Cited

U.S. PATENT DOCUMENTS

| | | |
|---|---|---|
| 7,499,745 B2 | 3/2009 | Littrup et al. |
| 7,783,344 B2 | 8/2010 | Lackey et al. |
| 7,801,591 B1 | 9/2010 | Shusterman |
| 7,844,325 B2 | 11/2010 | Takehara |
| 7,917,202 B2 | 3/2011 | Chamney et al. |
| 8,965,498 B2 | 2/2015 | Katra et al. |
| 9,727,702 B2 | 8/2017 | Kass-Hout et al. |
| 2006/0058593 A1 | 3/2006 | Drinan et al. |

(Continued)

*Primary Examiner* — Jon Eric C Morales
(74) *Attorney, Agent, or Firm* — Neo IP

(57) ABSTRACT

A health care management system for geospatial biosurveillance including a bioimpedance device. The health care management system provides real time data and analysis of an individual's physiological condition using bioimpedance data. The health care management system is further operable to monitor and model disease progression and remission based on physiological conditions during a pandemic event as well as modeling the treatment and remediation of long-lasting physiological symptoms and organ damage due to post-acute sequelae of SARS-CoV2 infection (PASC).

20 Claims, 9 Drawing Sheets

(56) References Cited

U.S. PATENT DOCUMENTS

| | | |
|---|---|---|
| 2016/0338639 A1 | 11/2016 | Myers et al. |
| 2018/0333107 A1 | 11/2018 | Sada et al. |
| 2018/0374582 A1 | 12/2018 | Holmes et al. |
| 2019/0357776 A1 | 11/2019 | Carreon et al. |
| 2021/0161403 A1* | 6/2021 | Beer .................... A61B 5/7282 |

* cited by examiner

GEOSPATIAL BIOIMPEDANCE BIOSURVEILLANCE TOOL

CROSS REFERENCES TO RELATED APPLICATIONS

This application claims priority to and the benefit of U.S. Provisional Application No. 63/016,475 filed Apr. 28, 2020, which is incorporated by reference in its entirety.

BACKGROUND OF THE INVENTION

1. Field of the Invention

The present invention relates to bioimpedance, and more specifically to using bioimpedance as a geospatial biosurveillance tool.

2. Description of the Prior Art

It is generally known in the prior art to provide impedance sensors for determining the physiological condition of an individual.

Prior art patent documents include the following:

US Patent Publication No. 2018/0374582 for integrated health data capture and analysis system by inventor Holmes et al., filed Apr. 13, 2018 and published Dec. 27, 2018, is directed to an integrated health care surveillance and monitoring system that provides real-time sampling, modeling, analysis, and recommended interventions. The system can be used to monitor infectious and chronic diseases. When faced with outbreak of an infectious disease agent, e.g., influenza virus, the system can identify active cases through pro-active sampling in high risk locations, such as schools or crowded commercial areas. The system can notify appropriate entities, e.g., local, regional and national governments, when an event is detected, thereby allowing for proactive management of a possible outbreak. The system also predicts the best response for deployment of scarce resources.

US Patent Publication No. 2019/0357776 for body state classification by inventor Carreon et al., filed Feb. 15, 2017 and published Nov. 28, 2019, is directed to system for determining reference signatures for use in assisting identification of a body state in a biological subject, the system including at least one processing device that obtains reference data for each of a plurality of reference individuals, the reference data including at least one reference impedance indicator obtained by performing at least one impedance measurement on the reference individual, a body state indication indicative of any body states associated with the reference individual and characteristic data indicative of one or more physical characteristics of the reference individual and analyses the reference data to establish one or more reference signatures, each reference signature being indicative of at least one reference impedance indicator associated with a respective body state for respective physical characteristics.

U.S. Pat. No. 9,727,702 for global disease surveillance platform, and corresponding system and method by inventor Kass-Hout et al., filed Oct. 24, 2011 and issued Aug. 8, 2017, is directed to a computer-implemented method for identifying and assessing public health events, and a corresponding system and apparatus, includes capturing public health-related information from structured and unstructured sources, where the information is contained in one or more documents, extracting meta-data from the captured public health-related information, creating an index of the extracted meta-data; archiving the meta-data and the documents, where the index links meta-data to its associated document, processing the extracted meta-data according to one or more detection algorithms to determine if an anomaly exists, and where an anomaly exists, providing a public health event notification, and monitoring and evaluating the responses to the public health events.

U.S. Pat. No. 7,801,591 for digital healthcare information management by inventor Shusterman, filed Dec. 20, 2006 and issued Sep. 21, 2010, is directed to a system for diagnosis, medical decision support, and healthcare information management that performs analysis of serial health data, adapts to the individual data, and represents dynamics of the most significant parameters (indicators), using at least two scales. The system uses the first-scale (low-resolution) analysis of a snapshot measurement of at least one indicator (primary element) such as heart rate or blood pressure and uses a second-scale (higher-resolution) analysis to determine serial changes in each of the said primary elements. The system optimizes information flow, usage of medical knowledge, and improves accuracy of analysis of serial changes, and adaptability to each individual's data. The information can be distributed in parallel to separate databases at different locations.

U.S. Pat. No. 7,783,344 for hydration monitoring by inventor Lackey et al., filed Aug. 20, 2004 and issued Aug. 24, 2010, is directed to systems and techniques for monitoring hydration. In one implementation, a method includes measuring an electrical impedance of a region of a subject to generate an impedance measurement result, and wirelessly transmitting the data to a remote apparatus. The probe with which impedance is measured may take the form of a patch adhesively secured to the subject.

U.S. Pat. No. 7,917,202 for method and a determining the hydration and/or nutrition status of patient by inventor Chamney et al, filed Jun. 29, 2004 and issued Mar. 29, 2011, is directed to monitoring the hydration and/or nutrition status of a patient by bioimpedance. A bioimpedance method and device that makes use of a refined model by which the conductivity contributions from intracellular tissues can be taken better into account to enable an improved assessment of the body composition of a patient with increased accuracy. The intracellular volume (ICV) of a patient is determined by determining an intracellular electrical resistance Rmix of the patient and deriving the intracellular volume ICV using Rmix by taking into account that a cell of a kind of tissue contributes differently to the electrical resistance Rmix of the intracellular volume ICV compared with a cell of a second kind of tissue. The application also relates to a device for carrying out the method according to the invention and to a computer program product to be used on such a device.

U.S. Pat. No. 8,965,498 for method and apparatus for personalized physiologic parameters by inventor Katra et al., filed Mar. 28, 2011 and issued Feb. 24, 2015, is directed to methods and apparatus combine patient measurement data with demographic or physiological data of the patient to determine an output that can be used to diagnose and treat the patient. A customized output can be determined based the demographics of the patient, physiological data of the patient, and data of a population of patients. In another aspect, patient measurement data is used to predict an impending cardiac event, such as acute decompensated heart failure. At least one personalized value is determined for the patient, and a patient event prediction output is generated based at least in part on the personalized value and the measurement data. For example, bioimpedance data may be used to establish a baseline impedance specific to the patient, and the patient event prediction output generated based in part on the relationship of ongoing impedance measurements to the baseline impedance. Multivariate prediction models may enhance prediction accuracy.

US Patent Publication No. 2006/0058593 for monitoring platform for detection, hemorrhage and blood loss by inventor Drinan et al., filed Sep. 2, 2005 and published Mar. 16, 2006, is directed to systems and techniques for monitoring hydration. In one implementation, a method includes measuring an electrical impedance of a region of a subject to generate an impedance measurement result. The result may be correlated with a blood loss condition.

U.S. Pat. No. 7,499,745 for multidimensional bioelectrical tissue analyzer by inventor Littrup et al., filed Feb. 27, 2001 and issued Mar. 3, 2009, is directed to a method and apparatus that use complex impedance measurements of tissue in human or animal bodies for the detection and characterization of medical pathologies. An analysis of the complex impedance measurements is performed by a trained evaluation system that uses a nonlinear continuum model to analyze the resistive, capacitive, and inductive measurements collected from a plurality of sensing electrodes. The analysis of the impedance measurements results in the construction of a multidimensional space that defines the tissue characteristics, which the trained evaluation system uses to detect and characterize pathologies. The method and apparatus are sufficiently general to be applied to various types of human and animal tissues for the analysis of various types of medical pathologies.

US Patent Publication No. 2018/0333107 for non-invasive wearable device, process and systems with adjustable operation by inventor Sada et al., filed May 16, 2018 and published Nov. 22, 2018, is directed to a wearable device for attachment to a body part of a user is for sensing, feedback and adjusting features. The wearable device includes a flexible housing, an array of sensing devices configured to be positioned proximate the body part to determine respective physiological characteristics of the user, and a processor configured to receive and process information regarding the physiological characteristics from the array of sensing devices. A communication module is associated with the processor and configured to communicate data to/from an external control unit (ECU). The processor is configured to receive adjustment signals from the ECU and adjust the sensing devices for performance control according to an image registration process that includes mapping a position and arrangement of the sensing devices relative to anatomical structures defined in an anatomical model to generate a mapped anatomical model, and generating tissue-related measurements within the mapped anatomical model based upon targeted anatomical structures within a sensitivity path relative to the sensing devices.

US Patent Publication No. 2016/0338639 for personal hydration monitor by inventor Myers et al., filed May 20, 2016 and published Nov. 24, 2016, is directed to various embodiments for a flexible hydration sensor that can be implemented in a wearable device. A hydration monitoring device can include at least one flexible electrode comprising a plurality of silver nanowires embedded within a polydimethylsiloxane (PDMS) substrate. Processing circuitry can be configured to measure a hydration level of an individual wearing the hydration monitoring device based at least in part on a measurement of a skin impedance of the individual. In some embodiments, the hydration monitoring device can also generate a hydration metric based on the level of hydration and display the hydration metric.

U.S. Pat. No. 7,844,325 for bioelectricity impedance measuring device, a malnutrition measurement system, a malnutrition measurement method by inventor Takehara et al., filed Jun. 4, 2008 and issued Nov. 30, 2010, is directed to a bioelectricity impedance measuring device includes a contact surface capable of being placed on a part of the body, a gripper which is formed to be easily grasped by a single hand, and electrodes on the contact surface. In addition, the bioelectricity impedance measuring device further includes a malnutrition measuring device which measures malnutrition. An operation and control device measures Phase angle theta and/or an RcXc ratio, and measures a nutrient state. The malnutrition measuring device measures the state of malnutrition from a value of Phase angle theta. A display shows the results of measurement with a bar classified by display of a color. In addition, the operation and control device further measures muscular volume. The operation and control device, by being capable of being provided data or regression, can also measure muscular volume for a child aged 5 or younger or an adult aged 60 or older.

SUMMARY OF THE INVENTION

The present invention relates to using bioimpedance as a geospatial biosurveillance tool.

It is an object of this invention to provide real-time continuous bioimpedance monitoring.

In one embodiment, the present invention includes a device for measuring bioimpedance.

In another embodiment, the present invention includes a system for health care data management including a wearable bioimpedance device.

In yet another embodiment, the present invention includes a method of monitoring physiological conditions using bioimpedance.

These and other aspects of the present invention will become apparent to those skilled in the art after a reading of the following description of the preferred embodiment when considered with the drawings, as they support the claimed invention.

DETAILED DESCRIPTION

Figure 1:
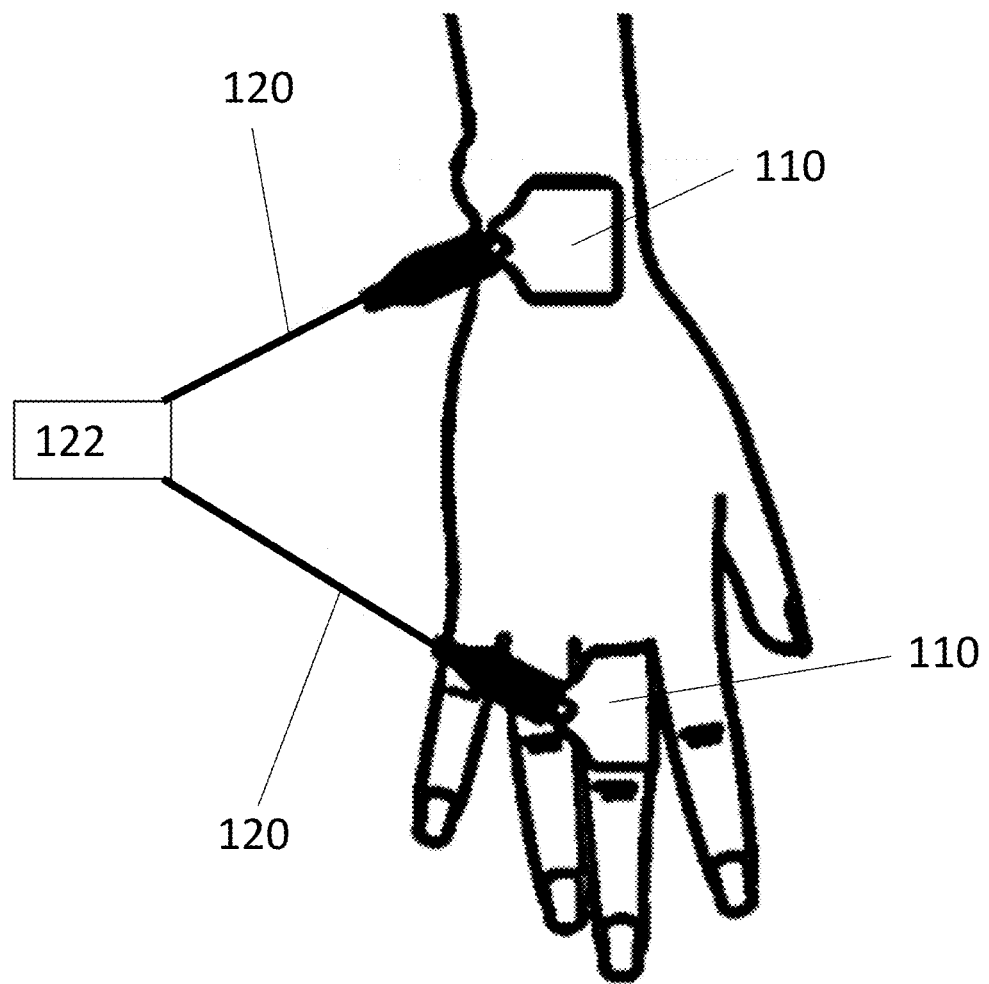
FIG. 1 illustrates an impedance device according to one embodiment of the present invention.

The present invention is generally directed to using impedance for geospatial biosurveillance.

In one embodiment, the present invention includes a device for measuring bioimpedance.

In another embodiment, the present invention includes a system for health care data management including a wearable bioimpedance device.

In yet another embodiment, the present invention includes a method of monitoring physiological conditions using bioimpedance.

None of the prior art discloses a healthcare system using bioimpedance as a geospatial biosurveillance tool.

Bioelectrical impedance analysis is used to verify body composition, prognosis of morbidity and comorbidity, and detect the percentage of fat mass and fat-free mass. The principle of bioelectrical impedance analysis is that the passage of an alternate electric current in a body finds resistance related to a subject's body composition. There is a direct relationship between the concentration of ions and the electrical conductivity and an indirect relationship between the ion concentration and the resistance of the solution. Impedance is defined as the opposition of a conductor to the flow of an alternating current. Body impedance is the amount of dropped voltage when a small constant current (ex. 800 uA) with a fixed frequency (ex. 50 kHz) passes between electrodes spanning the body. Body impedance consists of resistance and reactance. Resistance is the major opposition of the voltage and typically arises from extra cellular water and intracellular water. At a low frequency (ex. 50 kHz), the extra-cellular part of non-adipose tissue works as a resistor. Reactance is an additional opposition or the storage of an electrical charge by a condenser for a short period of time (ex. the lipid component of the membranes of a body cell mass which reduce the flow of intracellular ions). Reactance causes a delay in current flow produced by cell membranes and tissue interfaces. The delay in current flow creates a phase shift. The phase shift is quantified geometrically as the angular transformation of the capacitance to resistance ratio or phase angle.

Phase angle data improves the accuracy and efficiency of disease diagnosis and monitoring because it is a prognostic indicator of the outcomes of diseases. Phase angles are calculated by determining the arctangent of the reactance over the resistance and multiplying by 180 over pi. The numerical value can differ according to sex, age, body mass index, presence of disease, and other physiological conditions. Therefore, there is a need for a healthcare system that adapts phase angle analysis based on a user's symptoms and body characteristics.

Bioelectrical impedance analysis has two types: single-frequency and multi-frequency. For example, and not limitation, single-frequency analysis is performed at 50 kHz and the main resistance is offered by extracellular water and a low contribution of intracellular water. Multi-frequency analysis uses frequencies ranging from 5 to 500 kHz. When using a frequency less than 50 kHz, the estimated resistance is from the extracellular water. At higher frequencies, the analysis also evaluates the resistance of the intracellular water.

Many single and multiple-frequency bioimpedance analyses use a conductor-volume model and multiple regression analysis that results in large errors of prediction of total body water, extracellular water and fat free mass because the analyses rely on an assumption of a constant body composition. These errors can multiply in users that are characterized as fluid overloaded, dehydrated, or obese. Individuals have different body compositions and shapes, so using constant values for intracellular and extracellular resistivity only compounds inaccurate results and potentially can lead to a misdiagnosis. For example, resistivity measurements could indicate that a patient has COVID-19, when in actuality the patient has diabetes, heart failure, or another underlying condition. Therefore, a method is needed for collecting and monitoring the impedance level of a user without mathematical manipulation to provide accurate and real-time analysis of a user's condition. This would improve medical care for patients as it lowers the risk for improper diagnosis and provide real-time diagnosis.

Advantageously, bioelectrical impedance analysis is further operable to determine the hydration status and other fluid-related conditions of an individual. Current methods of determining fluid overload, fluid in the lungs, swelling in the lower legs and depression in the swollen area are done by physical elimination (ex. pressing a finger into the swelling and coring a pitting edema on a numerical scale). However, all of these methods are indirect, late, and fail to continuous monitor a patient's condition.

In addition, traditional methods of monitoring an individual's condition include blood studies, imaging techniques (ex. x-ray) and physical examination. However, these methods are expensive, whereas bioimpedance data can be obtained in an efficient manner while providing evidence of a change in an individual's condition. Changes in impedance values reflect the real-time change associated with the presence, progression and severity of disease. Also, many traditional methods require further evaluation to provide a full nutritional assessment using weight, diet, disease history, physical examination, anthropometric measurements, and/or an assessment of functional capacity. Therefore, there is a need for real-time, noninvasive, health care monitoring system to provide real-time diagnosis of an individual without requiring a full nutritional assessment.

In addition, there is a need to accurately identify malnutrition. Poor nutrition leads to altered body composition (ex. decreased lean body mass and body cell mass) and causes a decrease in physical and mental functions. The present invention illustrates the nutrition status of an individual in a single number and monitors the real-time changes in nutrition due to disease, treatment or compliance.

Lastly, there is a need for a reliable approach to monitoring and modeling disease progression, remission, and prognosis. The present invention includes continuous or near-continuous real-time impedance monitoring of multiple users at the same time that allows for tracking a disease on a global scale without causing an undue burden on users or healthcare providers. Furthermore, the continuous or near-continuous monitoring allows for data capture and analysis that would otherwise be impossible without a user going to a healthcare provider.

Referring now to the drawings in general, the illustrations are for the purpose of describing one or more preferred embodiments of the invention and are not intended to limit the invention thereto.

Figure 4:
FIG. 4 illustrates an impedance device according to one embodiment of the present invention.

FIG. 1 illustrates an impedance system according to one embodiment of the present invention. In one embodiment, the system includes at least one electrode 110 on the hands and wrist of a user. The system also includes a wire 120 connected to the at least one electrode 110. The wire 120 is further configured to connect to an electric device 122. In one embodiment, the electric device includes a power source, a current detection device and/or a remote device. In another embodiment, the wire 120 is configured to clip onto the at least one electrode 110. Alternatively, the at least one electrode 110 is located on a user's foot, ankle, leg, chest, torso and/or back. In yet another embodiment, the at least one electrode 110 comprises silver and chloride. In one embodiment, as illustrated in FIG. 4, the at least one electrode is attached on an individual's middle finger.

In one embodiment, the at least one electrode bisects the ulnar styloid process with the electrode tab facing away from the individual's body. The at least one electrode includes at least one signal induction electrode and at least one signal detection electrode. The at least one signal induction electrode is placed distally from the at least one signal detection electrode and the at least one signal induction electrode is at least equal distance away from the at least one signal distance electrode as the distance being measured (e.g. the wrist). In one embodiment, a signal induction electrode is placed on the distal phalanx of the middle finger. In another embodiment, the at least one signal detection electrode bisects the medial malleolus. The at least one signal induction electrode is placed on the hallux. Generally, the signal detection electrodes are placed superiorly and inferiorly based on the area of interest.

Figure 2:
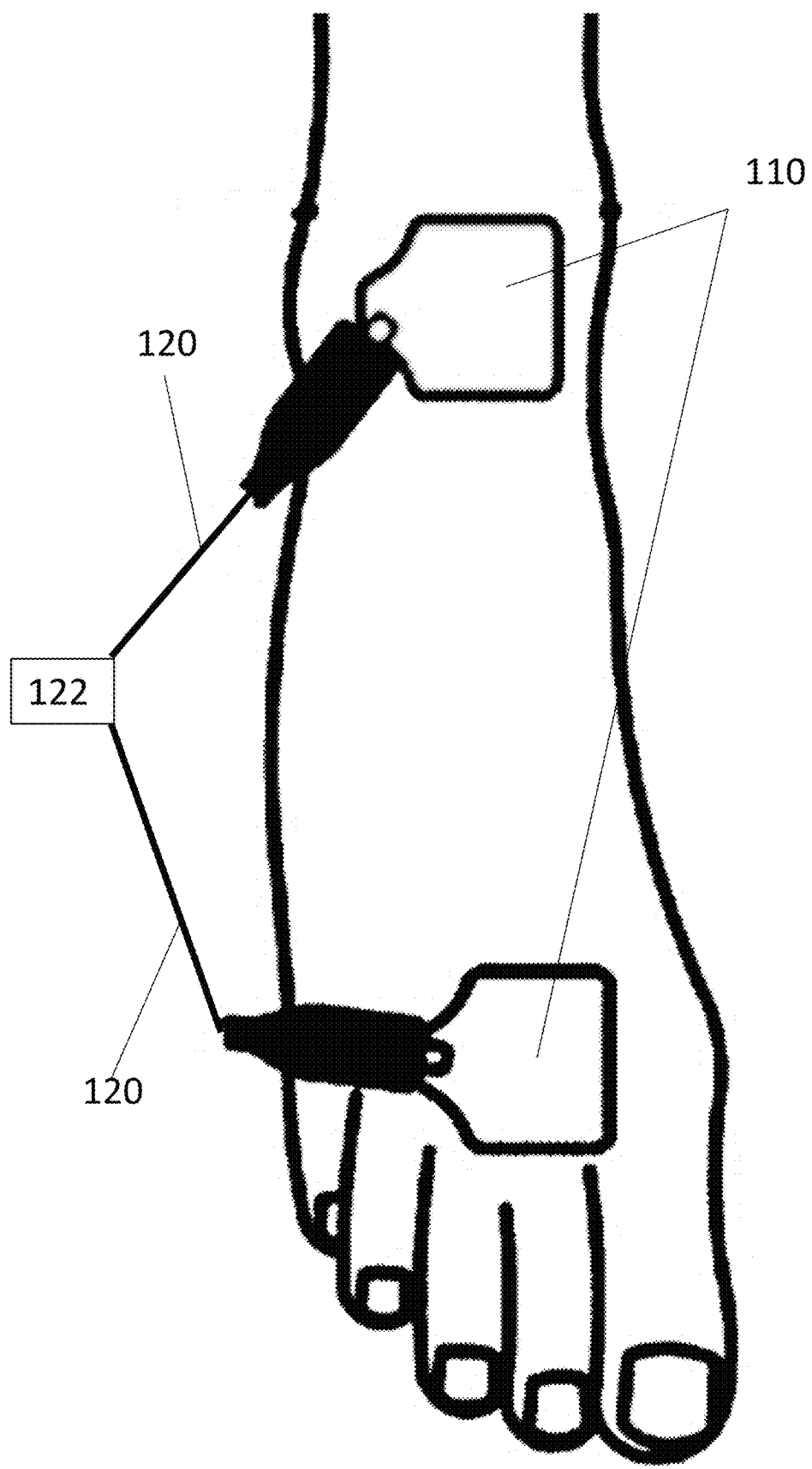
FIG. 2 illustrates an impedance device according to one embodiment of the present invention.
Figure 3:
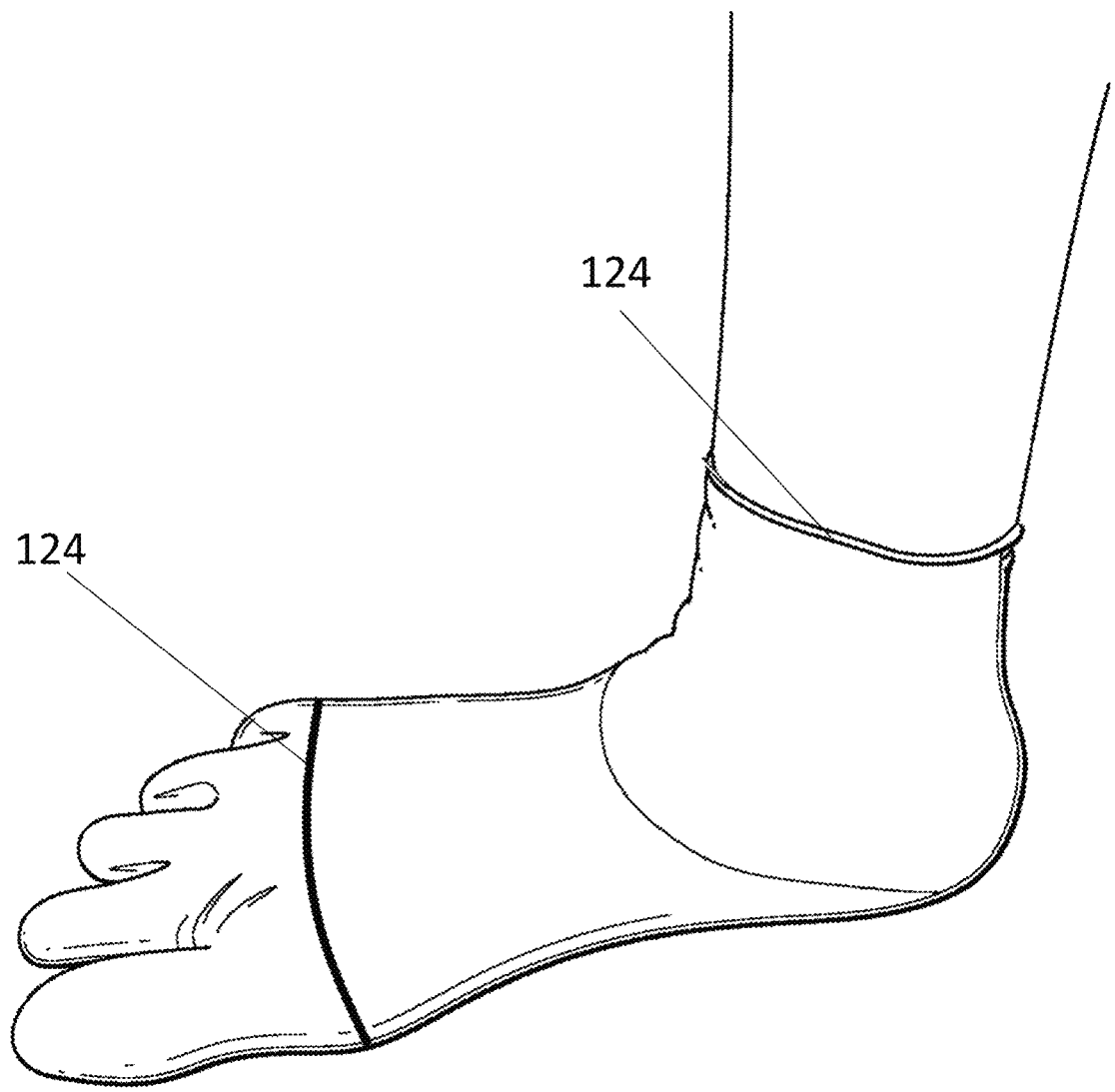
FIG. 3 illustrates an impedance device according to one embodiment of the present invention.

FIG. 2 illustrates an impedance device according to one embodiment of the present invention. The impedance device includes at least one electrode 110 on an individual's foot. In on embodiment, the at least electrode 110 is around a user's ankle and just beneath the toes on top of a user's foot. The impedance device includes a wire 120 that is connected to an electric device 122. In one embodiment, the electric device 122 includes a power source, a current detection device and/or a remote device. FIG. 3 illustrates an impedance device according to one embodiment of the present invention. In one embodiment, the impedance device includes at least one electrode 124 around the ankle of an individual and at least one electrode 124 wrapped around the foot. The present invention is operable for electrodes of differing thicknesses.

In another embodiment, the present invention includes at least one electrode measurement device. The at least one electrode measurement device is configured to measure the impedance value between the electrodes. The at least one electrode measurement device is configured for contact with an individual's body and to measure an electrical current transmitted between electrodes to determine an individual's impedance value.

In one embodiment, at least one electrode is placed on the hands and wrist. At least one remote device is configured to determine the impedance of a user based on the difference in voltage between the electrodes on a user's hands and wrists. In order to send an electric signal, the electrodes are energized. In one embodiment, the electrodes are connected to a battery, photocell, and/or a radio frequency identification tag (RFID) collecting device (ex. mobile device). In another embodiment, the electrodes are configured for wireless charging (ex. induction charging). The electrodes are configured to receive an energization signal from the at least one remote device. The electrodes are noninvasive and are configured to transmit single frequency and multi-frequency electric signals. In one embodiment, the electrodes are operable to transmit electrical signals between 5-500 kHz. The captured data is sent and displayed on the at least one remote device. In another embodiment, the captured data is uploaded to a cloud server.

The electrodes directly measure the electrical conductive properties of a user. The at least one remote device is further configured to determine fluid volume, cell mass and cell membranes without any mathematical or statistical manipulation. These measurements correspond to the hydration, nutrition status, prognosis and the timing of non-acute death. The at least one remote device is configured to track user data over time and analyze the progression of a user's health.

In yet another embodiment, the present invention includes an electrode device. The electrode device is configured to create an electrode as needed by an individual. The electrode device is operable to capture bioimpedance data between various parts of an individual. Advantageously, this allows for analysis of areas of interest of an individual.

In another embodiment, the present invention determines an impedance ratio using a multi-frequency bioimpedance analysis. The impedance ratio is measured between the impedance at 200 kHz and the impedance at 5 kHz. At 200 kHz, the total body water is measured and at 5 kHz, only extracellular water is measured. In healthy tissues, the ratio is less than 1. In a systemic illness, cell membranes can be disrupted, allowing protein leaks and fluids and electrolytes shift in extracellular space, which can be shown with an impedance ratio closer to 1.

In yet another embodiment, the present invention is used for military personnel. The bioimpedance system is configured to capture data for a multiplicity of users to monitor the performance of military personnel in real-time. The bioimpedance system is configured to analyze the vitality of military personnel. The vitality analysis includes monitoring the status of disease progression and/or monitoring recovery. Advantageously, the bioimpedance system is configured to generate a noise floor for the captured data. In one embodiment, the bioimpedance system is operable to recognize thermal noise, atmospheric noise, electronic noise, and other environmental and background noise that arise when using the bioimpedance system. The bioimpedance system is further configured to filter the environmental and background noise.

In one embodiment, the at least one remote device is configured to display the location and health status of military personnel. In one embodiment, each person appears as a dot or other icon on a map on the at least one remote device, and the health status and coordinates or other location data is operable to be displayed by hovering a cursor over the icon or through touch activation with the icon. In another embodiment, the location and health status is automatically displayed next to the icon. In yet another embodiment, the icons are color coded or include other visual representations to indicate health status. The health status includes nutrition status, hydration status, disease status and/or wound status. The at least one remote device is operable to select an individual military personnel via user input. The at least one remote device includes an artificial intelligence component that is operable to analyze and model a person's health. The artificial intelligence component enables real-time decision making for when military personnel need medical assistance and to evaluate the condition of a battle unit during a battle. Advantageously, this prevents military personnel from being pushed too far as well as allowing for real-time updates on the condition of a battle.

In yet another embodiment, the present invention includes a wearable bioimpedance device. As shown the FIG. 4, in one embodiment, the wearable bioimpedance device includes a glove. The glove includes at least one electrode 125 on the finger portion of the glove and at least one electrode 125 on the wrist. The glove further includes an energizing component on the wrist. The glove is configured to connect to another wearable bioimpedance device (ex. glove) and then transmits captured data via mobile communications. Advantageously, this allows for military personnel to wear flame retardant gloves while monitoring bioimpedance.

Figure 5:
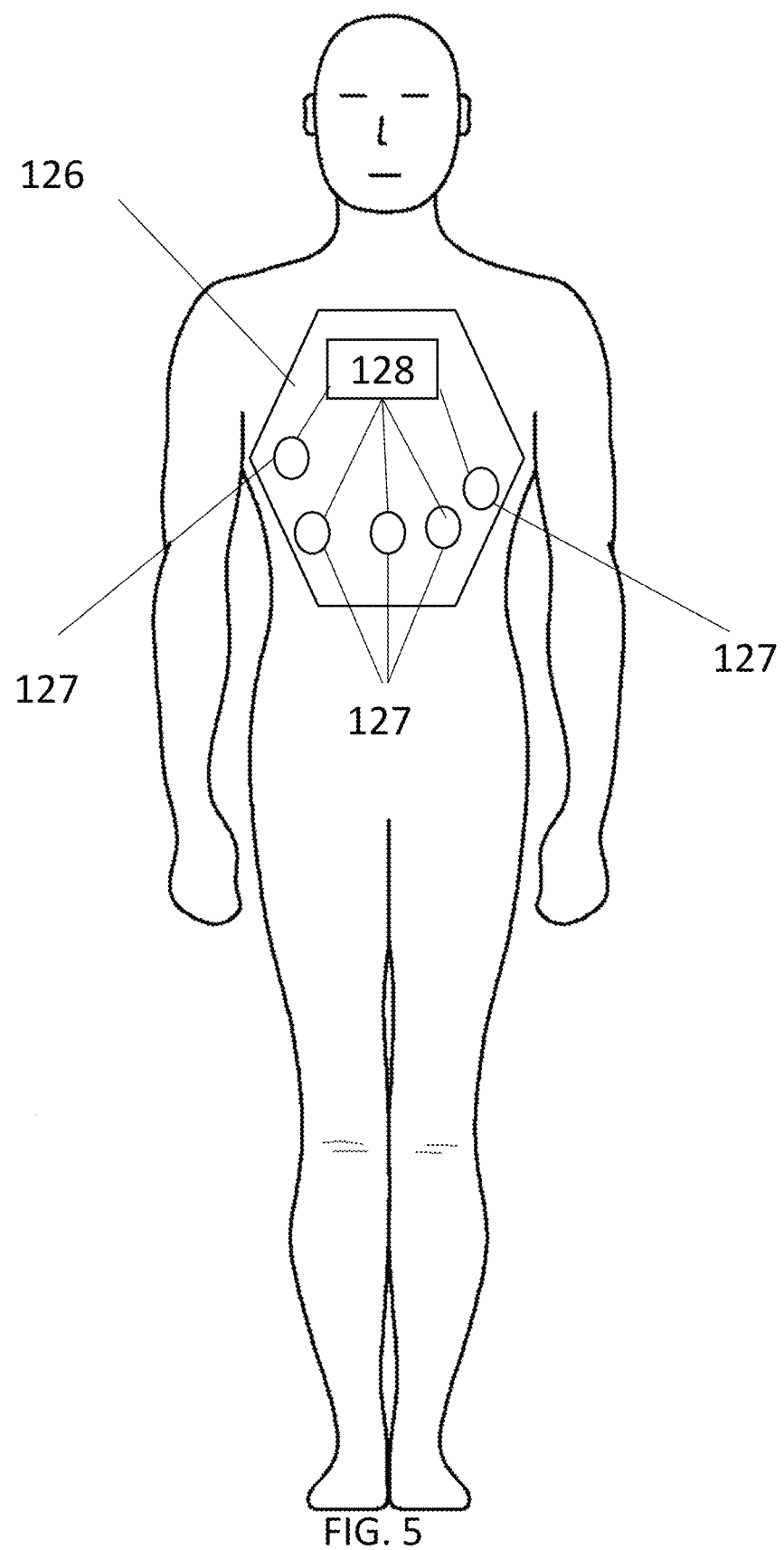
FIG. 5 illustrates an impedance device according to one embodiment of the present invention.

FIG. 5 illustrates a bioimpedance device according to one embodiment of the present invention. The bioimpedance device includes a wearable patch 126. The wearable patch 126 includes at least one sensor 127 and a remote device 128 attached to the patch. In one embodiment, the at least one sensor 127 includes an ECG sensor, a temperature sensor, a sweat sensor and other body sensors.

Figure 6:
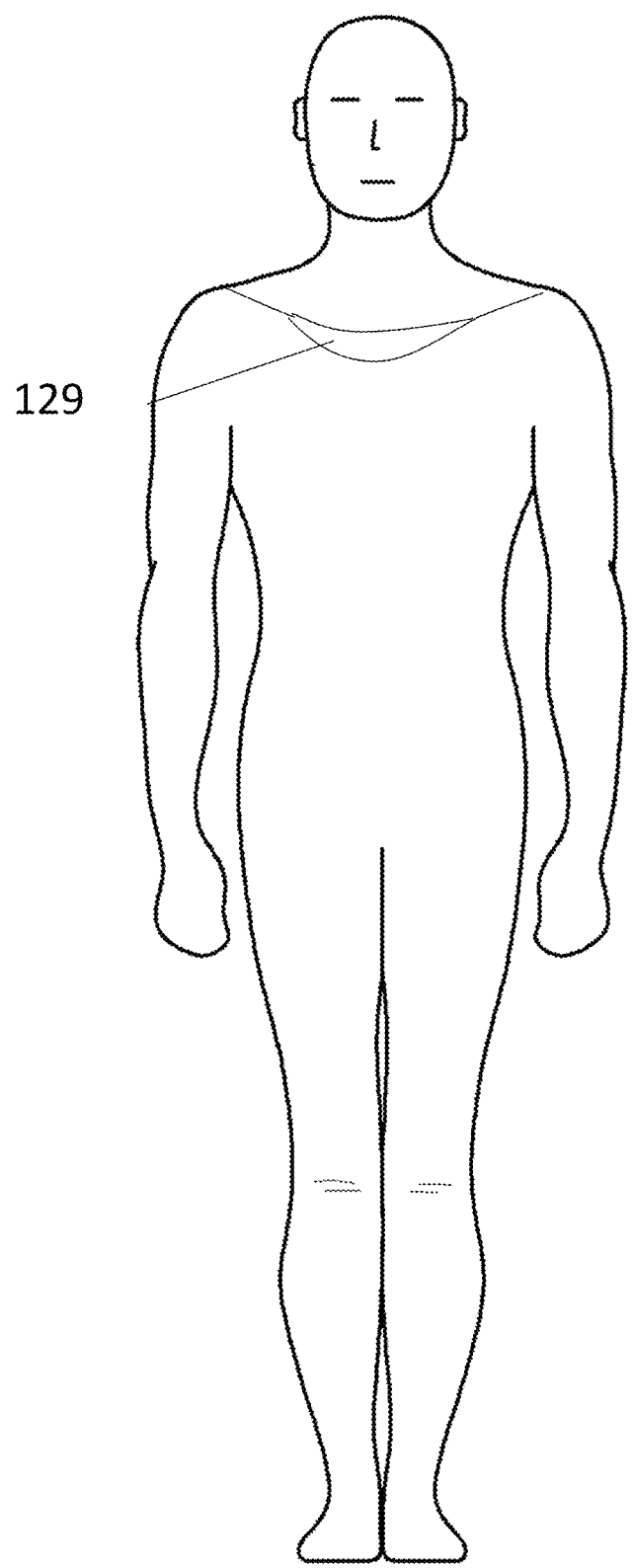
FIG. 6 illustrates an impedance device according to one embodiment of the present invention.

FIG. 6 illustrates a bioimpedance device according to one embodiment of the present invention. In one embodiment, the present invention includes a neck gaiter 129. The neck gaiter 129 includes an electrode at the base of the neck. In yet another embodiment, the impedance device is a hand-to-hand device. In one embodiment, the hand-to-hand device includes an electronic device. The electronic device includes an embedded chip that is configured to collect and transmit an individual's data. Advantageously, the electronic device is configured to display a user's health status and alert an individual if they need to see a medical professional.

Figure 7:
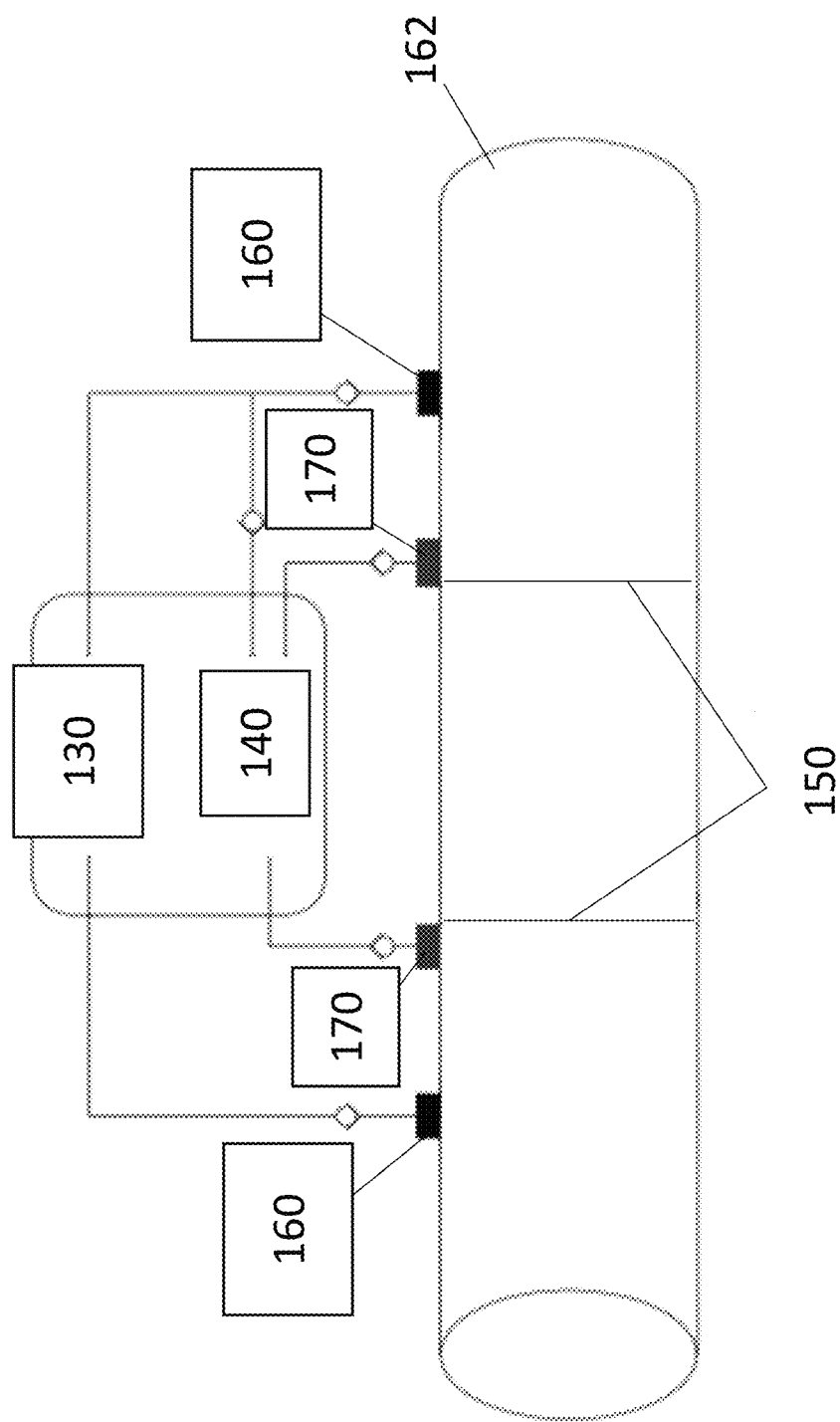
FIG. 7 illustrates a device subject interface according to one embodiment of the present invention.

FIG. 7 illustrates a device user interface according to one embodiment of the present invention. The device-subject interface includes a current source 130, a measurement component 140, and an area of interest 150. The current source 130 transmits an electric current between two signal introduction points 160. The signal introduction points 160 are located on a user's body 162. The measurement component 140 is located between two signal detection points 170. The area of interest 150 is located between the two signal detection points 170. In one embodiment, a current source 130 is applied at two signal introduction points 160. A measurement component 140 is placed in between the signal introduction points 160. The measurement component 140 captures the electrical field distribution between an area of interest 150 between the signal introduction points 160. The electrical field data is transmitted from the measurement component 140 to at least one remote device. The at least one remote device is configured to analyze the electrical field data to determine the impedance of a user.

In one embodiment, the present invention includes a health care management system. The health care management system includes a wearable bioimpedance device, a server, and at least one remote device. The health care system includes a user's history, status, actions and in actions. A user's medical history includes social and psychological history to establish potential effects of living conditions, loneliness and depression on nutritional needs. Nutrition history is also included, with limitations on food intake, to help decide the underlying nutritional causes. The wearable bioimpedance device is configured to transmit data to the server and to the at least one remote device via any communication protocol known in the art, including but not limited to cellular communications such as 3G, 4G, 5G, etc., satellite communications, and/or any other wireless communication. In one embodiment, the wearable bioimpedance device includes a display and the wearable bioimpedance device is configured to display a user's health data on the display. Alternatively, the remote device includes a display and is configured to display a user's health information. In yet another embodiment, the wearable bioimpedance device is configured to be charged via a wired or wireless connection with a battery source. The wearable bioimpedance device is powered by a battery while operating. In another embodiment, the wearable bioimpedance device includes a radio-frequency identification (RFID) tag. The RFID tag is powered by an electromagnetic source and is operable to transmit data via wireless communication (ex. Bluetooth). In another embodiment, the RFID tag is powered by a battery. In yet another embodiment, the RFID tag is disposable. The health care management system is operable to identify when a RFID tag needs to be charged or replaced. Advantageously, the health care management system is configured to transmit an alert to the remote device and/or the wearable bioimpedance device to charge and/or replace the electrode. The wearable impedance device includes a bracelet, a watch, a cuff, an armband, a leg band, chest band and other similar wearable devices. Alternatively, the health care system includes a hand held impedance device. This allows for a user to travel with the device without having to keep the impedance device on the user's body.

In one embodiment, the health care management system uses body resistance and reactance values derived from a 50 kHz signal and generates an impedance vector. The impedance vector is inversely related to the total body water. The combination of the impedance vector length and direction is the phase angle and is used to indicate the tissue hydration status. A decreased phase angle is an indicator of prognosis of illnesses. Phase angles are sensitive to alterations in tissue electrical properties, and early disturbances in cell membrane function are identified by longitudinal decrease in phase angle values. Therefore, the phase angles provide a real-time insight on the condition of a user and increase the likelihood of a proper diagnosis and earlier response times.

In yet another embodiment, the system is operable to determine body parameters of a user from the impedance data. Body parameters include body cell mass, fat free mass, fat mass, nutrition status, fitness level, extracellular mass, water retention, and total body water. The impedance data includes reactance values. The reactance values are proportional to the integrity of cell wall membranes. For example, and not limitation, the reactance values are useful for analyzing skeletal musculature organs such as the liver, spleen, lungs, heart, stomach and intestines. Increased membrane and anabolic metabolism are shown by an increase of reactance, which indicates an improvement of a user's health. A rapid decrease in reactance provides indication of condition that rapidly affect cells (ex. Rhabdomyolysis)

The health care management system is operable to diagnose and provide recommendations for diseases. By way of example and not limitation, diagnosable diseases include COVID-19, post-acute COVID-19 syndrome, cachexia, malnutrition, oncologic diseases, HIV infection, AIDS, HCV, viral, bacterial, fungal, and parasitic infections, cholera, diabetes mellitus, congestive heart failure, multiple sclerosis, rheumatoid arthritis, obesity, lymphedema, liver cirrhosis, chronic obstructive pulmonary disease, hemodialysis, and sepsis. Impedance measurements are related to biomarkers associated with inflammation such as CRP and IL-6 and suggest the presence of cytokine storm syndrome which can result in adult respiratory distress syndrome and multi-organ failure. Therefore, the present invention is further operable to identify inflammation, respiratory distress syndrome and multi-organ failure.

In one embodiment, the health care management system is further configured to determine the health of the endocannabinoid system. The health care management system is further configured to detect endocannabinoids. Endocannabinoids include endogenous lipids, derivatives of amides, esters, and ethers, and long-chain polyunsaturated fatty acids. The present invention is operable to detect and monitor levels of anandamide (AEA) and 2-arachidonoylglycerol (2-AG). In yet another embodiment, the present invention is configured to detect the mRNA levels of cannabinoid receptors, CB1, CB2, and CB3. If endocannabinoid function is decreasing, then the present invention is configured to examine to see if a user is experiencing other symptoms such as derangements of digestion, mood, and sleep. Advantageously, the present invention is operable to provide at least one recommendation to improve a user's condition if the user is experiencing a decrease in endocannabinoid system activity.

In another embodiment, the present invention includes an artificial intelligence component on a remote server. The remote server is configured to receive the impedance data and other data related to the user in addition to data from third-party sources. The artificial intelligence component is configured to detect and model correlations between the data captured from a user and the disease and/or symptoms the user is experiencing based on the impedance data and the data from the third-party sources.

The health care management system is further configured to diagnose a condition which affects serum electrolytes, hematocrit and blood flow. In response to a diagnosis, the server is configured to capture information from third-party data sources. The server is configured to send the information to an artificial intelligence component of the health care management system. The artificial intelligence component is operable to generate a recommended health care plan in response to the diagnosis and the third-party data.

The artificial intelligence component is further configured to identify a continuous geomap of an individual. The artificial intelligence component is further configured to identify changes of an individual, particularly as a result of exercise, dehydration and malnutrition. The artificial intelligence component is operable to filter noise from electrical values associated with individuals and identify readings that indicate changes from a healthy baseline. This allows for the health care management to capture bioimpedance data while an individual is moving. Ideally, an individual is lying down when bioimpedance data is being collected, however, this is not always possible. Therefore, the artificial intelligence component is configured to determine and filter electrical noise associated with movement and other factors affecting data collection in order to provide real-time continuous bioimpedance monitoring.

Advantageously, the artificial intelligence component is further configured to access a database of ICD-10 codes and suggest recommend at least one ICD-10 status based on an individual's data. The artificial intelligence component is further operable to learn about a patient's comorbidity, drug regimen, genetics, demographics, nutrition and exercise. The bioimpedance data is specific for both whole body measurements and hand-to-hand measurements. The summation of the bioimpedance data will include the effects of the disease on the individual's body and the artificial intelligence component is configured to analysis the effect of a disease on an individual.

Advantageously, the bioimpedance system is configured to calculate muscle mass. In addition, the bioimpedance system is operable to monitor wound healing. In one embodiment, the at least one electrode is placed near the wound to enable longitudinal monitoring of the directional changes in resistance values. Resistance is inversely related to extracellular fluid volume and to fibrin clot formation. An increase in reactance indicates epidermal proliferation and granulation of the wound. Therefore, a positive slope for resistance values indicates healing whereas a negative slope indicates complications such as infection. For example, and not limitation, a decrease in resistance indicates a cell drying where as an increase in resistance indicates fluid accumulation. A decrease in resistance and impedance indicates inflammation and a rapid decrease in resistance and reactance indicates an infection.

In another embodiment, the electrodes are movable, so a user can position an electrode to monitor a particular wound. The health care management system includes at least one remote device that alerts a user to the correct placement of electrodes. This is particularly useful for military applications because it allows military personnel to monitor a wound while in a remote location with little to zero medical support. Furthermore, if the electrodes are in an incorrect position then the system cannot generate an accurate health status. By notifying a user of an incorrect electrode position, the health care management system is lowering the risk of improper diagnosis and improving the health monitoring of users.

Typically, a scab will form over a wound, thereby making it difficult to determine the healing progression of the wound. A sample of the wound bed would normally be taken with a swab and a laboratory test would be performed on the collected sample. However, the present invention overcomes the disadvantages of prior art by providing noninvasive bioimpedance monitoring of a wound. Wounds heal from the inside out so the bioimpedance data generates a curve that indicates whether or not the cells are still breaking down and if there is an improvement with the health of a wound. Advantageously, this allows for remote, continuous monitoring of a wound without visiting a healthcare provider.

In yet another embodiment, the bioimpedance system includes an artificial intelligence component that is operable to determine when the electrodes are in the wrong location and/or have been moved. Generally, the longer the distance between the two measurement points, the larger the measured resistance will be. So, if one or both measurement electrodes are placed too far apart, then too large values of the resistances will be measured, which results in too low estimates on fluid volumes. Inversely, if the electrodes are placed too closed together, then the measurements will give too low values of the resistances and too high estimates of fluid volumes. When high-frequency current flows in a too large fluid volume during the measurement (ex. two legs instead of one), then the reported fluid volume will naturally be too large. Advantageously, the bioimpedance system is operable to determine when the received impedance data is due to an error and generate an alert to a user.

In yet another embodiment, the present invention is directed to prognosis of a disease. The present invention overcomes the inaccuracies of statistically based methods of prior art. The health care management system provides non-invasive impedance analysis of a cell membrane structure, including a phase angle. The health care management system is operable to use the phase angle and the changes in phase angle to determine a user's vitality and frailty. Additionally, once the health care management system has determined that a disease is in remission and/or a user has fully recovered, then the system is configured to detect the presence of antibodies. The health care management system will generate an alert about the presence of antibodies and compare the number of antibodies across a multiplicity of users. This enables the bioimpedance system to model the recovery rate and risk that an individual may get sick again.

Additionally, the present invention is configured to recommend a medical care plan. For example, and not limitation, when the system determines an individual is suffering from malnourishment, the impedance system is configured to provide a recommended nutritional care plan. The nutritional care plan includes energy, nutrient and fluid requirements, nutrition goals, therapy, monitoring and assessment parameters. Nutritional care includes meal service, forms of nutrition, nutrient delivery, and nutrition education. Nutrition monitoring includes whether the requirements of liquid, energy and protein are being met, and if weight, fat free mass or fat mass are changing as expected.

Advantageously, the health care management system is operable to monitor disease progression and model an infection scenario using phase angles, impedance ratio and other biological information. Additionally, the health care management system is further configured to monitor for blood loss, diarrhea, and vomiting. The artificial intelligence component is operable to check for false alerts and heart failure. The health care management system is operable to track the progression of a user's physiological condition (ex. disease symptoms) in relation to time, location, and demographic information. Therefore, the present invention allows for accurate, real-time monitoring and diagnosis instead of waiting for a multiplicity of test results that would most likely require further examination and analysis.

In another embodiment, the health care management system includes an analytics platform. The analytics platform includes edge computing resources. The analytics platform is operable to identify and monitor trends in bioimpedance (ex. increase or decrease phase angles). Advantageously, the system is configured to correlate presymptomatic cellular degradation and presymptomatic indication of health status. The system further recommends and administers therapies at an earlier stage, preferably before symptoms of a disease occur, due to the analysis of the trends of the bioimpedance data.

The health care management system is operable to utilize a plurality of learning techniques including, but not limited to, machine learning (ML), artificial intelligence (AI), deep learning (DL), neural networks (NNs), artificial neural networks (ANNs), support vector machines (SVMs), Markov decision process (MDP), and/or natural language processing (NLP). The health care management system is operable to use any of the aforementioned learning techniques alone or in combination.

Further, the health care management is operable to utilize predictive analytics techniques including, but not limited to, machine learning (ML), artificial intelligence (AI), neural networks (NNs) (e.g., long short term memory (LSTM) neural networks), deep learning, historical data, and/or data mining to make future predictions and/or models. The health care management system is preferably operable to recommend and/or perform actions based on historical data, external data sources, ML, AI, NNs, and/or other learning techniques. The health care management system is operable to utilize predictive modeling and/or optimization algorithms including, but not limited to, heuristic algorithms, particle swarm optimization, genetic algorithms, technical analysis descriptors, combinatorial algorithms, quantum optimization algorithms, iterative methods, deep learning techniques, and/or feature selection techniques.

Alternatively, the health care management system is operable to analyze and monitor a multiplicity of users with one remote device. The multiplicity of users have at least one wearable bioimpedance device that transmits health characteristics to the remote device. The remote device is operable to identify a user based on individual health characteristics. Advantageously, this allows for remote monitoring in places with a large multiplicity of users (ex. hospitals or nursing homes) from one device. In yet another embodiment, the present invention is capable of modeling virtual herd immunity. Virtual herd immunity involves monitoring a multiplicity of individuals and determining which individuals of the multiplicity of individuals are immune to a disease. The present invention is operable to use bioimpedance data to determine the presence of antibodies in an individual. The artificial intelligence component is configured to compare bioimpedance data between individuals to determine healthy individuals without antibodies, sick individuals, and health individual with antibodies. This enables the present invention to accurately modeling of the progression of a disease in a population as well as identification of sick individuals that need to be quarantined.

In one embodiment, the wearable bioimpedance device is disposable. Alternatively, the wearable impedance device includes an adhesive band. The adhesive band is configured to wrap around an individual's finger and/or wrist. Then, a glove is placed over the adhesive band and electrical contact is created between the adhesive band and the glove. The wearable bioimpedance device is configured to collect bioimpedance data via the electrical contact with the adhesive band.

In another embodiment, the present invention includes a method of monitoring a user's health. Using a wearable bioimpedance device, a direct measurement of the electrical conductive properties of a user is captured. The user data is continuously captured, updated in real-time, and transmitted to a server. The server includes an artificial intelligence component that is configured to determine the hydration status, nutrition status and prognosis of a user's condition. Furthermore, the artificial intelligence component evaluates the response to treatments and is configured to provide an updated treatment plan.

The bioimpedance device of the present invention is advantageously operable to provide for continuous or near-continuous monitoring of a user. In the context of the present application, "continuous" or "near-continuous" measurements mean measurements taken every microsecond, every second, every minute, every few minutes, every hour, etc. By way of example, measurements are taken every microsecond, every two microseconds, every five microseconds, every ten microseconds, every fifty microseconds, every 100 microseconds, every 500 microseconds, every second, every five seconds, every ten seconds, every fifteen seconds, every thirty seconds, every minute, every two minutes, every five minutes, every ten minutes, every fifteen minutes, etc. By taking measurements of users regularly and consistently over a time period and in real-time or near real-time, the present invention provides for creating a complete profile of a user and determining impacts of events such as drinking a glass of water, sleeping, exercising, etc. on bioimpedance readings. These events are important in establishing a baseline for a user and understanding typical deviations from the baseline, and aid in the diagnosis of a disease by determining whether deviations from the baseline are normal or warrant further testing or treatment. The artificial intelligence component on the server is operable to establish a baseline from a group of measurements. The artificial intelligence component is operable to extrapolate future physiological and biological characteristics of a user such that if measurements are not obtained of a user for a period of time, the present invention is operable to determine a range of normal measurements for the user and quickly determine if the user has a disease or another health issue upon bioimpedance measurements being taken of the user after a period of no measurements.

The present invention also includes a database on the server in one embodiment. Data in the database includes medical data, body data, geographic data, nutrition data, military data, and environment data. Preferably, the data in the database is anonymized and is sortable by a variety of factors. Advantageously, the database is operable to be updated with diagnosis information and analysis of data in the database obtained before the diagnosis is operable to be utilized to help predict the onset of the disease in other users, including by way of example and not limitation, age, gender, race, ethnicity, lifestyle habits (ex. alcohol, physical activity, tobacco use, diet), blood pressure, blood sugar, cholesterol, weight loss, religion, employment status, and body mass index. The data is also operable to be normalized for certain patient groups, including groups of patients in an age range, of a certain ethnicity, with certain lifestyle habits, with certain biological measurements, etc. The present invention is operable to analyze the captured data and determine comorbidities and the effects of medications or groups of medication on certain groups of users within the database, as well as to predict the effects of medication or the likelihood of a diagnosis for members of the groups of users or other groups.

In one embodiment, the blockchain is used to anonymize data and provide an immutable record of measurements of a user. Advantageously, a single reading or data point can be compared with historical data based on the blockchain record of data for a user or a plurality of users. Additionally, the blockchain is used to track medical supplies and food; this is particularly advantageous in military applications. The present invention is configured to identify when an individual is experiencing malnutrition and/or needs medical treatment. After determining the condition and needs of an individual, the present invention is further configured to determine the location of medical supplies and food. The present invention is further operable to identify when food and medicals supplies need to be delivered and to generate an alert to deliver the supplies of food and pharmaceuticals. Advantageously, the blockchain increases the security for communication. It eliminates the risk associated with a central control because it verifies transactions between peer-to-peer networks and eliminates single points of failure. Therefore, the location of medical supplies and food is not risk to a security breach, which is especially advantageous for military applications as the transportation of supplies is critical to success.

In another embodiment, the blockchain is used as a surveillance platform for a multiplicity of users. The blockchain supports remote user monitoring with biosensors. The health care system is configured to identify and track public health emergencies. By way of example and not limitation, the public health emergencies include the spread of a disease and drug misuse/abuse. Advantageously, the blockchain identifies where a disease started and identifies at-risk individuals. The health care management system is further configured to capture and transmit real time data on vaccinations, antibiotics and/or other disease control data. The disease control data preferably includes the effectiveness of the treatments. Alternatively, the blockchain identifies and tracks healthy individuals while monitoring high-risk areas. The health care system is configured to generate an alert when a healthy individual has traveled through a high risk area. This increases the awareness of potential exposure to diseases and lowers the spread of infectious diseases because the present invention identifies areas with a low number of sick individuals and provides alerts if a sick individual is traveling.

In another embodiment, the blockchain is used to track an individual's health. The health care management system is configured to track an individual's health, to receive input on how the individual feels, and the amount of food, drinks, sleep, rest, and exercise that a user has had. The system includes an artificial intelligence component that is configured to filter deviations from an individual's normal or expected characteristics. The health care management system is further configured to correlate deviations from an individual's normal or expected characteristics with depressed phase angles for a disease state.

Figure 8:
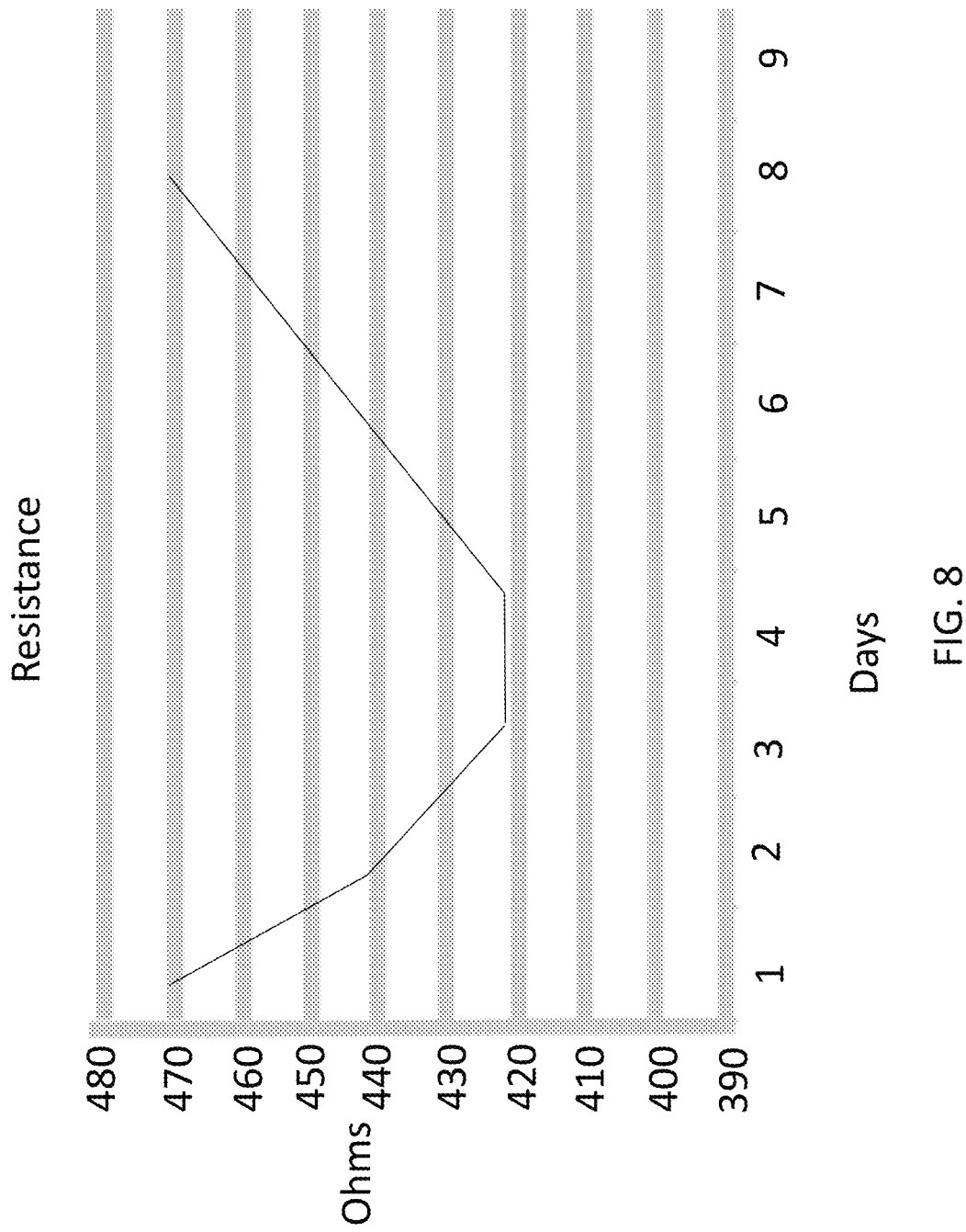
FIG. 8 illustrates a graphical representation of fluid tracking using a bioimpedance system according to one embodiment of the present invention.

FIG. 8 illustrates a graphical representation of measurements taken by a fluid tracking system according to one embodiment of the present invention. Preferably, the graphical representation of measurements is available via an application such as a mobile application or a desktop application for an individual user such that the user can track their own data and is alerted to any deviations from a baseline. The impedance system is configured to generate a graphical representation of a user's condition. For example, and not limitation, the first point is a baseline value of a user's physiological condition. The downward trend indicates fluid accumulation. Towards days 3 and 4, the rate of diminution is slowed and the value plateaus. The resistance value increases as fluid decrease and the user eventually returns to a normal value, indicating an improvement in the user's condition.

In another embodiment, the present invention is directed towards tracking the geolocation of an individual. The health care management system is operable to include individual data. The individual data includes demographic data, location data, nutrition data, and medical data. The health care management system is configured to create a map using a geographic location of an individual. In one embodiment, each individual is color coded based on the individual's health status. For example, and not limitation, an individual may be colored red if they are demonstrating symptoms of a disease. Advantageously, the present invention further includes a blockchain. The blockchain is configured to allow the present invention to use the individual data without disclosing the name and similar demographic information of an individual.

For additional information regarding bioimpedance including resistance, reactance and phase angle for assessment of prognosis, effectiveness of treatment and timing of non-acute death in an individual patient, see U.S. Pat. Nos. 6,587,715, 7,003,346, and 7,136,697, which are incorporated by reference in their entirety.

Location data is created in the present invention using one or more hardware and/or software components. By way of example and not limitation, location data is created using the Global Positioning System (GPS), low energy BLUETOOTH based systems such as beacons, wireless networks such as WIFI, Radio Frequency (RF) including RF Identification (RFID), Near Field Communication (NFC), magnetic positioning, and/or cellular triangulation. By way of example, location data is determined via an Internet Protocol (IP) address of a device connected to a wireless network. A wireless router is also operable to determine identities of devices connected to the wireless network through the router, and thus is operable to determine the locations of these devices through their presence in the connection range of the wireless router.

Figure 9:
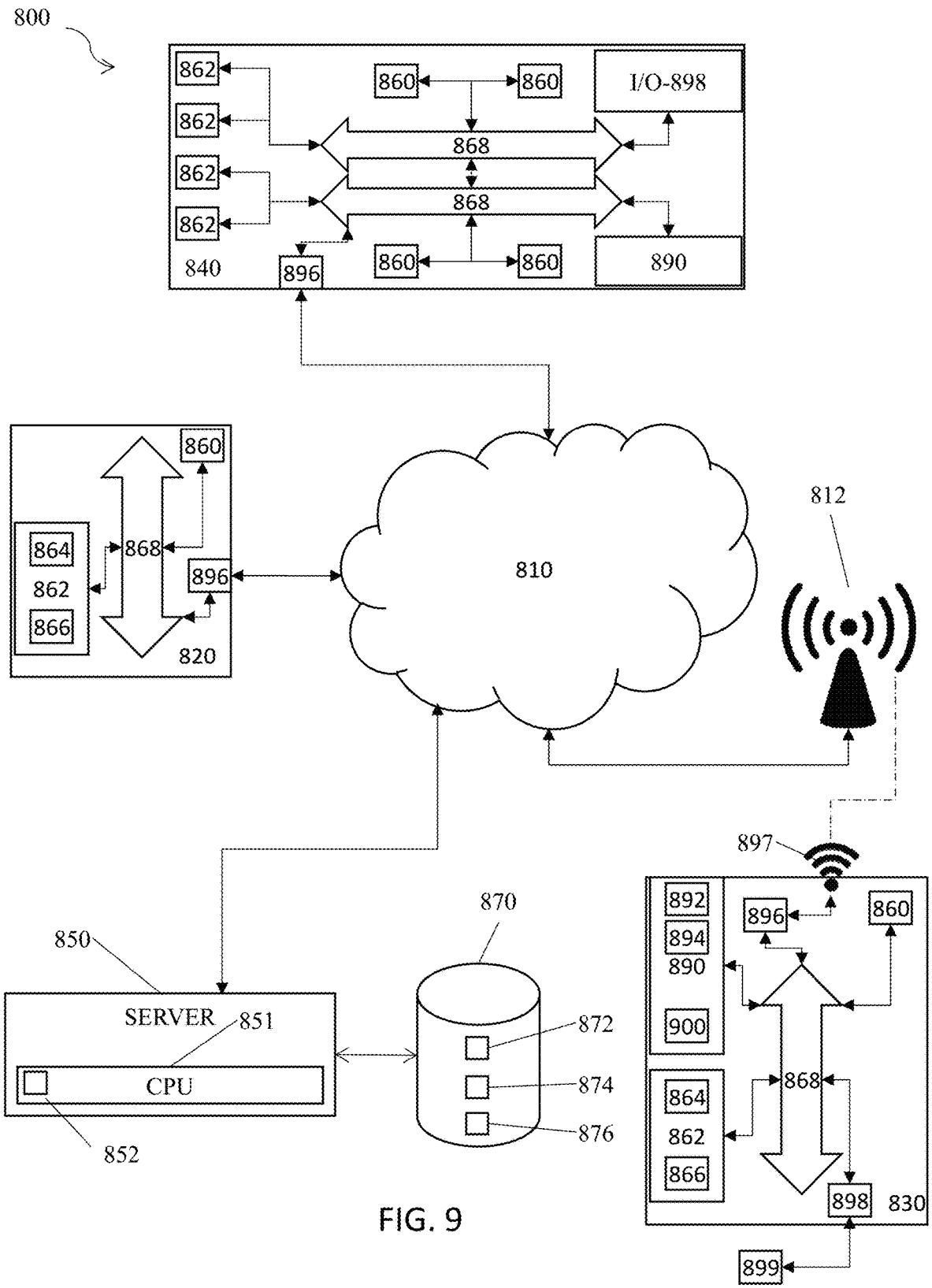
FIG. 9 is a schematic diagram of a system of the present invention.

FIG. 9 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 is operable to house an operating system 872, memory 874, and programs 876.

In one embodiment of the invention, the system 800 includes a network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 is operable to be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of electronic devices including at least a processor and a memory, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in the present application.

In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 is operable to additionally include components such as a storage device 890 for storing the operating system 892 and one or more application programs 894, a network interface unit 896, and/or an input/output controller 898. Each of the components is operable to be coupled to each other through at least one bus 868. The input/output controller 898 is operable to receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 is operable to be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 9, multiple processors 860 and/or multiple buses 868 are operable to be used, as appropriate, along with multiple memories 862 of multiple types (e.g., a combination of a DSP and a microprocessor, a plurality of microprocessors, one or more microprocessors in conjunction with a DSP core).

Also, multiple computing devices are operable to be connected, with each device providing portions of the necessary operations (e.g., a server bank, a group of blade servers, or a multi-processor system). Alternatively, some steps or methods are operable to be performed by circuitry that is specific to a given function.

According to various embodiments, the computer system 800 is operable to operate in a networked environment using logical connections to local and/or remote computing devices 820, 830, 840 through a network 810. A computing device 830 is operable to connect to a network 810 through a network interface unit 896 connected to a bus 868. Computing devices are operable to communicate communication media through wired networks, direct-wired connections or wirelessly, such as acoustic, RF, or infrared, through an antenna 897 in communication with the network antenna 812 and the network interface unit 896, which are operable to include digital signal processing circuitry when necessary. The network interface unit 896 is operable to provide for communications under various modes or protocols.

In one or more exemplary aspects, the instructions are operable to be implemented in hardware, software, firmware, or any combinations thereof. A computer readable medium is operable to provide volatile or non-volatile storage for one or more sets of instructions, such as operating systems, data structures, program modules, applications, or other data embodying any one or more of the methodologies or functions described herein. The computer readable medium is operable to include the memory 862, the processor 860, and/or the storage media 890 and is operable be a single medium or multiple media (e.g., a centralized or distributed computer system) that store the one or more sets of instructions 900. Non-transitory computer readable media includes all computer readable media, with the sole exception being a transitory, propagating signal per se. The instructions 900 are further operable to be transmitted or received over the network 810 via the network interface unit 896 as communication media, which is operable to include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

In one embodiment, the computer system 800 is within a cloud-based network. In one embodiment, the server 850 is a designated physical server for distributed computing devices 820, 830, and 840. In one embodiment, the server 850 is a cloud-based server platform. In one embodiment, the cloud-based server platform hosts serverless functions for distributed computing devices 820, 830, and 840.

In another embodiment, the computer system 800 is within an edge computing network. The server 850 is an edge server, and the database 870 is an edge database. The edge server 850 and the edge database 870 are part of an edge computing platform. In one embodiment, the edge server 850 and the edge database 870 are designated to distributed computing devices 820, 830, and 840. In one embodiment, the edge server 850 and the edge database 870 are not designated for distributed computing devices 820, 830, and 840. The distributed computing devices 820, 830, and 840 connect to an edge server in the edge computing network based on proximity, availability, latency, bandwidth, and/or other factors.

It is also contemplated that the computer system 800 is operable to not include all of the components shown in FIG. 9, is operable to include other components that are not explicitly shown in FIG. 9, or is operable to utilize an architecture completely different than that shown in FIG. 9. The various illustrative logical blocks, modules, elements, circuits, and algorithms described in connection with the embodiments disclosed herein are operable to be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

The above-mentioned examples are provided to serve the purpose of clarifying the aspects of the invention, and it will be apparent to one skilled in the art that they do not serve to limit the scope of the invention. By nature, this invention is highly adjustable, customizable and adaptable. The above-mentioned examples are just some of the many configurations that the mentioned components can take on. All modifications and improvements have been deleted herein for the sake of conciseness and readability but are properly within the scope of the present invention.

The invention claimed is:

1. A system for continuous or near continuous impedance monitoring of a user comprising:
   at least two electrodes;
   at least one bioelectric impedance device including a power source and a current detection component; and
   at least one remote device including an analytics platform;
   wherein the at least one bioelectric impedance device is in network communication with the at least one remote device;
   wherein the at least two electrodes are in contact with the user;
   wherein at least one electrode of the at least two electrodes bisects the ulnar styloid process of the user and at least one different electrode of the at least two electrodes is positioned on the distal phalanx of the middle finger of the user;
   wherein the at least one bioelectric impedance device is configured to generate current between the at least two electrodes via a wired connection or a wireless connection;
   wherein the at least one bioelectric impedance device is configured to capture impedance data of the user based on a voltage difference between the at least two electrodes, wherein the impedance data includes resistance data and reactance data;
   wherein the at least one remote device is configured to receive the impedance data from the at least one bioelectric impedance device, and wherein the at least one remote device is configured to generate phase angle data based on the impedance data;
   wherein the at least one remote device is configured to generate health status data based on the impedance data and phase angle data;
   wherein the at least one remote device is configured to determine if the user is affected by a disease based on the impedance data and the phase angle data; and
   wherein the at least one remote device is configured to monitor a progression of the disease based on the impedance data and the phase angle data.

2. The system of claim 1, wherein the at least two electrodes are configured for wireless charging, wherein the at least two electrodes are configured to receive an energization signal from the at least one remote device.

3. The system of claim 1, wherein the at least one remote device includes a display, wherein the at least one remote device is configured to track the location of the user via the at least one bioelectric impedance device, wherein the at least one remote device is configured to display the location and health status of the user.

4. The system of claim 1, wherein the system is further configured to identify when the user is affected by a disease, wherein the disease includes at least one of COVID-19, endocannabinoid system deficiency, cachexia, malnutrition, oncologic diseases, HIV infection, AIDS, HCV, viral, bacterial, fungal, and parasitic infections, cholera, diabetes mellitus, congestive heart failure, multiple sclerosis, rheumatoid arthritis, obesity, lymphedema, liver cirrhosis, chronic obstructive pulmonary disease, hemodialysis, inflammation, cytokine storm syndrome, organ failure, Parkinson's disease, migraines and/or sepsis.

5. A system for continuous or near continuous impedance monitoring of a plurality of users comprising:
   a bioelectric impedance device;
   at least one remote device; and
   at least one remote server including an analytics platform;
   wherein the bioelectric impedance device is positioned on each user of the plurality of users;
   wherein the bioelectric impedance device, the at least one remote device, and the at least one remote server are in network communication;
   wherein the bioelectric impedance device is configured to capture impedance data for the plurality of users, wherein the impedance data includes resistance data and reactance data;
   wherein the at least one remote device is configured to generate phase angle data based on the impedance data;
   wherein the at least one remote device is configured to determine if each user of the plurality of users is suffering from a disease;
   wherein the at least one remote server is configured to store historical data; wherein the historical data includes medical historical data and nutritional historical data of the plurality of users;
   wherein the analytics platform is configured to generate a baseline physiological condition for each user of the plurality of users;

wherein the at least one remote device is configured to determine the tissue hydration status of at least one user of the plurality of users based on the impedance data and the phase angle data;

wherein the at least one remote device is configured to monitor a progression of the disease for each user of the plurality of users based on the impedance data and the phase angle data; and wherein the at least one remote server is configured to generate an alert when a physiological condition of at least one user of the plurality of users exceeds at least one threshold from the baseline physiological condition of the at least one user of the plurality of users.

6. The system of claim 5, wherein the at least one remote device is configured to determine fluid volume, cell mass, and cell membrane integrity of the at least one user of the plurality of users based on the impedance data, wherein the analytics platform is configured to track the changes in the fluid volume, cell mass, and cell membrane integrity of the at least one user of the plurality of users over time, wherein the analytics platform is further configured to correlate the changes in the fluid volume, cell mass, and cell membrane integrity of the at least one user of the plurality of users with the progression of the disease.

7. The system of claim 5, wherein the at least one remote device is configured to determine at least one body parameter of each user of the plurality of users, wherein the at least one body parameter includes body cell mass, fat free mass, fat mass, nutrition status, fitness level, extracellular mass, water retention, and/or total body water.

8. The system of claim 5, wherein the at least one remote device is configured to detect antibodies based on the impedance data for each user of the plurality of users, wherein the analytics platform is further configured to model herd immunity based on the detection of antibodies for each user of the plurality of users.

9. The system of claim 5, wherein the at least one remote device is configured to track the geolocation of the plurality of users via the bioelectric impedance device, wherein the at least one remote device includes a display, and wherein the at least one remote device is configured to create a map using the geolocation of the plurality of users, wherein the at least one remote device is configured to color code each user of the plurality of users based on the health status data, wherein the health status data includes nutrition data and hydration data.

10. The system of claim 5, wherein the at least two electrodes are placed on opposite sides of a wound, wherein the impedance data includes directional changes of the resistance data, wherein the system is configured for longitudinal monitoring of the directional changes of the resistance data, wherein the at least one remote device is configured to determine the status of the wound based on the changes in the resistance data.

11. A system for continuous or near continuous impedance monitoring of a user comprising:
at least two electrodes;
at least one bioelectric impedance device including a power source and a current detection component; and
at least one remote device including an analytics platform;
wherein the at least one bioelectric impedance device is in network communication with the at least one remote device;
wherein the at least two electrodes are in contact with the user;

wherein the at least two electrodes include at least one signal detection electrode and at least one signal induction electrode, wherein the at least one signal detection electrode bisects the medial malleolus of the user and the at least one signal induction electrode is positioned on the hallux of the user;

wherein the at least one bioelectric impedance device is configured to generate current between the at least two electrodes via a wired connection or a wireless connection;

wherein the at least one bioelectric impedance device is configured to capture impedance data of the user based on a voltage difference between the at least two electrodes, wherein the impedance data includes resistance data and reactance data;

wherein the at least one remote device is configured to receive the impedance data from the at least one bioelectric impedance device, and wherein the at least one remote device is configured to generate phase angle data based on the impedance data;

wherein the at least one remote device is configured to generate health status data based on the impedance data and phase angle data;

wherein the at least one remote device is configured to determine if the user is affected by a disease based on the impedance data and the phase angle data; and wherein the at least one remote device is configured to monitor the progression of the disease based on the impedance data and the phase angle data.

12. The system of claim 11, further including a remote server including an artificial intelligence component, wherein the artificial intelligence component is configured to provide at least one recommendation for the user, wherein the at least one recommendation includes at least one time and at least one location to provide medical assistance.

13. The system of claim 11, further including a remote server including an artificial intelligence component, wherein the artificial intelligence component is configured to generate a physiological condition for the user, wherein the artificial intelligence component is configured to provide at least one alert when the physiological condition of the user is demonstrating signs of illness and/or disease, wherein the at least one alert is transmitted to the at least one remote device.

14. The system of claim 11, wherein the at least one bioelectric impedance device includes at least one of a glove, a band, or a patch, wherein the at least one bioelectric impedance device further includes at least one body sensor.

15. The system of claim 11, wherein the at least one remote device is configured to determine at least one body parameter of the user, wherein the at least one body parameter includes body cell mass, fat free mass, fat mass, nutrition status, fitness level, extracellular mass, water retention, and/or total body water.

16. The system of claim 11, wherein the at least one remote device is further configured to identify when the user is affected by a disease, wherein the disease includes at least one of COVID-19, post-acute COVID-19 syndrome, cachexia, endocannabinoid system deficiency, malnutrition, oncologic diseases, Human Immunodeficiency virus (HIV) infection, acquired immune deficiency syndrome (AIDS), Hepatitis C (HCV), viral, bacterial, fungal, and parasitic infections, cholera, diabetes mellitus, congestive heart failure, multiple sclerosis, rheumatoid arthritis, obesity, lymphedema, liver cirrhosis, chronic obstructive pulmonary disease, hemodialysis, Parkinson's disease, organ failure, migraines, and/or sepsis.

17. The system of claim 11, further including at least one remote server including an artificial intelligence component, wherein the at least one remote server is configured to receive third-party data from at least one third-party data source via network communication, wherein the at least one remote server is configured to generate a health care plan in response to the impedance data and the third-party data.

18. The system of claim 11, further including at least one remote server including an artificial intelligence component, wherein the at least one remote server is configured to receive the impedance data, the phase angle data, and the health status data for the user, wherein the artificial intelligence component is configured to determine and model trends between the impedance data, the phase angle data, and the health status data prior to the user being affected by the disease, during the progression of the disease, and during recovery.

19. The system of claim 11, wherein the at least one remote device is configured to detect antibodies based on the impedance data for the user.

20. The system of claim 11, wherein the at least one remote device is configured to track the geolocation of the user via the at least one bioelectric impedance device, wherein the at least one remote device includes a display, and wherein the at least one remote device is configured to create a map using the geolocation of the user, wherein the at least one remote device is configured to color code the user based on the health status data, wherein the health status data includes nutrition data and hydration data.

\* \* \* \* \*